US007588902B2

(12) United States Patent
Katze et al.

(10) Patent No.: US 7,588,902 B2
(45) Date of Patent: Sep. 15, 2009

(54) METHODS AND COMPOSITIONS FOR DIAGNOSING HEPATOCELLULAR CARCINOMA

(75) Inventors: Michael Katze, Seattle, WA (US); Roger Bumgarner, Kenmore, WA (US); Mariya Smit, Mukilteo, WA (US); Gary Rosenberg, Danbury, CT (US)

(73) Assignee: Illumigen Biosciences, Inc., Seattle, WA (US)

( * ) Notice: Subject to any disclaimer, the term of this patent is extended or adjusted under 35 U.S.C. 154(b) by 143 days.

(21) Appl. No.: 10/520,322

(22) PCT Filed: Jul. 3, 2003

(86) PCT No.: PCT/US03/20841

§ 371 (c)(1),
(2), (4) Date: Oct. 27, 2005

(87) PCT Pub. No.: WO2004/005466

PCT Pub. Date: Jan. 15, 2004

(65) Prior Publication Data

US 2007/0161058 A1 Jul. 12, 2007

Related U.S. Application Data

(60) Provisional application No. 60/393,982, filed on Jul. 3, 2002.

(51) Int. Cl.
*G01N 33/53* (2006.01)

(52) U.S. Cl. .................. 435/7.23; 436/501; 436/518

(58) Field of Classification Search .................. None
See application file for complete search history.

(56) References Cited

U.S. PATENT DOCUMENTS

2004/0068096 A1    4/2004   Tsuchihashi et al.

FOREIGN PATENT DOCUMENTS

| EP | 0334962 B1 | 4/1995 |
|----|------------|--------|
| EP | 1217033    | 6/2002 |
| WO | WO 98/55508 | 12/1998 |
| WO | WO 03/062395 A3 | 7/2003 |
| WO | WO 03/083046 A2 | 10/2003 |
| WO | WO 2004/005466 A3 | 1/2004 |

OTHER PUBLICATIONS

Fan et al., 1992, J Cancer Res Clin Oncol, vol. 118, pp. 371-376.*
Rouault et al., Oct. 7, 2003 vol., 42, issue 39, pp. 11494-11503.*
Smith et al., Cancer Research, Feb. 15, 2003;63(4):859-64.*
Rouault et al., 2003, Biochemistry, vol. 42, pp. 11494-11503.*
Lin et al., Clinical Aspects of Hepatocellular Carcinoma: Role of Serum C-Reactive Protein as a Marker of Hepatocellular Carcinoma in Patents with Cirrhosis, Journal of Gastroenterology and Hepatology, 2000, 417-421, vol. 15.
Smith et al., Identification of Novel Tumor Markers in Hepatitis C Virus-Associated Hepatocellular Carcinoma, Cancer Research, Feb. 2003, 859-864, vol. 63.
Takahashi et al., Expression of Telomerase Component Genes in Hepatocellular Carcinoma, Eur. J. Cancer; Mar. 2000, 496-502, vol. 36.
Trojan et al., Fluorine-18 FDG Position Emission Tomography for Imaging of Hepatocellular Carcinoma, Am. J. Gastoenterol., Nov. 1999, 3314-3319, vol. 94.
Niet et al., *International Journal of Cancer* 94:492-499 (2001), p. 492 Materials and Methods, p. 497 Discussion, 2nd and third paragraphs.
Fujiyama, S., et al., "Clinical Evaluation of Plasma Abnormal Prothrombin (PIVKA-II) in Patients with Hepatocellular Carcinoma," Hepato-gastroenterol 33: 201-205, 1986.
Pirisi, Mario, et al., "Increased Serum Phospholipase A2 Activity in Advanced Chronic Liver Disease as an Expression of the Acute Phase Response," Disease Markers 11: 103-111, 1993.
Shimizu, A., et al., "Sequential Fluctuation Pattern of Serum des-gamma-carboxy prothrombin Levels Detected by High-Sensitive Electrochemiluminescence System as an Early Predictive Marker for Hepatocellular Carcinoma in Patients with Cirrhosis," International Journal of Molecular Medicine 9: 245-250, 2002.

* cited by examiner

*Primary Examiner*—Misook Yu
(74) *Attorney, Agent, or Firm*—K&L Gates LLP

(57) ABSTRACT

Methods for the diagnosis of hepatocellular carcinoma (HCC) are set forth. Improved assay methods and scanning methods are included that employ non-cell-associated and cell-associated HCC related proteins. Such methods are based upon the discovery of genes that were up-regulated in diseased versus normal tissue as well as in HCC tissue when compared to the tissue of patients with other ailments.

3 Claims, No Drawings

SEQUENCE LISTING

<160> NUMBER OF SEQ ID NOS: 16

<210> SEQ ID NO 1
<211> LENGTH: 195
<212> TYPE: PRT
<213> ORGANISM: Homo sapiens

<400> SEQUENCE: 1

```
Met Lys Leu Ala Ser Gly Phe Leu Val Leu Trp Leu Ser Leu Gly Gly
 1               5                  10                  15

Gly Leu Ala Gln Ser Asp Thr Ser Pro Asp Thr Glu Glu Ser Tyr Ser
                20                  25                  30

Asp Trp Gly Leu Arg His Leu Arg Gly Ser Phe Glu Ser Val Asn Ser
            35                  40                  45

Tyr Phe Asp Ser Phe Leu Glu Leu Leu Gly Gly Lys Asn Gly Val Cys
        50                  55                  60

Gln Tyr Arg Cys Arg Tyr Gly Lys Ala Pro Met Pro Arg Pro Gly Tyr
65                  70                  75                  80

Lys Pro Gln Glu Pro Asn Gly Cys Gly Ser Tyr Phe Leu Gly Leu Lys
                85                  90                  95

Val Pro Glu Ser Met Asp Leu Gly Ile Pro Ala Met Thr Lys Cys Cys
                100                 105                 110

Asn Gln Leu Asp Val Cys Tyr Asp Thr Cys Gly Ala Asn Lys Tyr Arg
            115                 120                 125

Cys Asp Ala Lys Phe Arg Trp Cys Leu His Ser Ile Cys Ser Asp Leu
        130                 135                 140

Lys Arg Ser Leu Gly Phe Val Ser Lys Val Glu Ala Ala Cys Asp Ser
145                 150                 155                 160

Leu Val Asp Thr Val Phe Asn Thr Val Trp Thr Leu Gly Cys Arg Pro
                165                 170                 175

Phe Met Asn Ser Gln Arg Ala Ala Cys Ile Cys Ala Glu Glu Glu Lys
                180                 185                 190

Glu Glu Leu
        195
```

<210> SEQ ID NO 2
<211> LENGTH: 194
<212> TYPE: PRT
<213> ORGANISM: Homo sapiens

<400> SEQUENCE: 2

```
Met Lys Leu Ala Ser Gly Phe Leu Val Leu Trp Leu Ser Leu Gly Gly
 1               5                  10                  15

Gly Leu Ala Gln Ser Asp Thr Ser Pro Asp Thr Glu Glu Ser Tyr Ser
                20                  25                  30

Asp Trp Gly Leu Arg His Leu Arg Gly Ser Phe Glu Ser Val Asn Ser
            35                  40                  45
```

```
Tyr Phe Asp Ser Phe Leu Glu Leu Leu Gly Gly Lys Asn Gly Val Cys
     50                  55                  60

Gln Tyr Arg Cys Arg Tyr Gly Lys Ala Pro Met Pro Arg Pro Gly Tyr
 65                  70                  75                  80

Lys Pro Gln Glu Pro Asn Gly Cys Gly Ser Tyr Phe Leu Gly Leu Lys
                 85                  90                  95

Val Pro Glu Ser Met Asp Leu Gly Ile Pro Ala Met Thr Lys Cys Cys
            100                 105                 110

Asn Gln Leu Asp Val Cys Tyr Asp Thr Cys Gly Ala Asn Lys Tyr Arg
        115                 120                 125

Cys Asp Ala Lys Phe Arg Trp Cys Leu His Ser Ile Cys Ser Asp Leu
130                 135                 140

Lys Arg Ser Leu Gly Phe Val Ser Lys Val Glu Ala Cys Asp Ser Leu
145                 150                 155                 160

Val Asp Thr Val Phe Asn Thr Val Trp Thr Leu Gly Cys Arg Pro Phe
                165                 170                 175

Met Asn Ser Gln Arg Ala Ala Cys Ile Cys Ala Glu Glu Glu Lys Glu
            180                 185                 190

Glu Leu

<210> SEQ ID NO 3
<211> LENGTH: 464
<212> TYPE: PRT
<213> ORGANISM: Homo sapiens

<400> SEQUENCE: 3

Met Tyr Ser Asn Val Ile Gly Thr Val Thr Ser Gly Lys Arg Lys Val
1               5                  10                  15

Tyr Leu Leu Ser Leu Leu Leu Ile Gly Phe Trp Asp Cys Val Thr Cys
                 20                  25                  30

His Gly Ser Pro Val Asp Ile Cys Thr Ala Lys Pro Arg Asp Ile Pro
             35                  40                  45

Met Asn Pro Met Cys Ile Tyr Arg Ser Pro Glu Lys Lys Ala Thr Glu
 50                  55                  60

Asp Glu Gly Ser Glu Gln Lys Ile Pro Glu Ala Thr Asn Arg Arg Val
 65                  70                  75                  80

Trp Glu Leu Ser Lys Ala Asn Ser Arg Phe Ala Thr Thr Phe Tyr Gln
                 85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220
```

```
Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
            245                 250                 255

Trp Lys Ser Lys Phe Ser Pro Glu Asn Thr Arg Lys Glu Leu Phe Tyr
        260                 265                 270

Lys Ala Asp Gly Glu Ser Cys Ser Ala Ser Met Met Tyr Gln Glu Gly
    275                 280                 285

Lys Phe Arg Tyr Arg Arg Val Ala Glu Gly Thr Gln Val Leu Glu Leu
290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
            325                 330                 335

Gln Glu Trp Leu Asp Glu Leu Glu Glu Met Met Leu Val Val His Met
        340                 345                 350

Pro Arg Phe Arg Ile Glu Asp Gly Phe Ser Leu Lys Glu Gln Leu Gln
    355                 360                 365

Asp Met Gly Leu Val Asp Leu Phe Ser Pro Glu Lys Ser Lys Leu Pro
370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
            405                 410                 415

Ser Thr Ala Val Val Ile Ala Gly Arg Ser Leu Asn Pro Asn Arg Val
        420                 425                 430

Thr Phe Lys Ala Asn Arg Pro Phe Leu Val Phe Ile Arg Glu Val Pro
    435                 440                 445

Leu Asn Thr Ile Ile Phe Met Gly Arg Val Ala Asn Pro Cys Val Lys
450                 455                 460

<210> SEQ ID NO 4
<211> LENGTH: 2463
<212> TYPE: PRT
<213> ORGANISM: Homo sapiens

<400> SEQUENCE: 4

His Ile Asn Ile Asp Gln Phe Val Arg Lys Tyr Arg Ala Ala Leu Gly
1               5                   10                  15

Lys Leu Pro Gln Gln Ala Asn Asp Tyr Leu Asn Ser Phe Asn Trp Glu
            20                  25                  30

Arg Gln Val Ser His Ala Lys Glu Lys Leu Thr Ala Leu Thr Lys Lys
        35                  40                  45

Tyr Arg Ile Thr Glu Asn Asp Ile Gln Ile Ala Leu Asp Asp Ala Lys
    50                  55                  60

Ile Asn Phe Asn Glu Lys Leu Ser Gln Leu Gln Thr Tyr Met Ile Gln
65                  70                  75                  80

Phe Asp Gln Tyr Ile Lys Asp Ser Tyr Asp Leu His Asp Leu Lys Ile
            85                  90                  95

Ala Ile Ala Asn Ile Ile Asp Glu Ile Ile Glu Lys Leu Lys Ser Leu
            100                 105                 110

Asp Glu His Tyr His Ile Arg Val Asn Leu Val Lys Thr Ile His Asp
        115                 120                 125

Leu His Leu Phe Ile Glu Asn Ile Asp Phe Asn Lys Ser Gly Ser Ser
    130                 135                 140
```

-continued

```
Thr Ala Ser Trp Ile Gln Asn Val Asp Thr Lys Tyr Gln Ile Arg Ile
145                 150                 155                 160

Gln Ile Gln Glu Lys Leu Gln Leu Lys Arg His Ile Gln Asn Ile
                165                 170                 175

Asp Ile Gln His Leu Ala Gly Lys Leu Lys Gln His Ile Glu Ala Ile
            180                 185                 190

Asp Val Arg Val Leu Leu Asp Gln Leu Gly Thr Thr Ile Ser Phe Glu
        195                 200                 205

Arg Ile Asn Asp Val Leu Glu His Val Lys His Phe Val Ile Asn Leu
    210                 215                 220

Ile Gly Asp Phe Glu Val Ala Glu Lys Ile Asn Ala Phe Arg Ala Lys
225                 230                 235                 240

Val His Glu Leu Ile Glu Arg Tyr Glu Val Asp Gln Gln Ile Gln Val
                245                 250                 255

Leu Met Asp Lys Leu Val Glu Leu Thr His Gln Tyr Lys Leu Lys Glu
            260                 265                 270

Thr Ile Gln Lys Leu Ser Asn Val Leu Gln Gln Val Lys Ile Lys Asp
        275                 280                 285

Tyr Phe Glu Lys Leu Val Gly Phe Ile Asp Asp Ala Val Lys Lys Leu
    290                 295                 300

Asn Glu Leu Ser Phe Lys Thr Phe Ile Glu Asp Val Asn Lys Phe Leu
305                 310                 315                 320

Asp Met Leu Ile Lys Lys Leu Lys Ser Phe Asp Tyr His Gln Phe Val
                325                 330                 335

Asp Glu Thr Asn Asp Lys Ile Arg Glu Val Thr Gln Arg Leu Asn Gly
            340                 345                 350

Glu Ile Gln Ala Leu Glu Leu Pro Gln Lys Ala Glu Ala Leu Lys Leu
        355                 360                 365

Phe Leu Glu Glu Thr Lys Ala Thr Val Ala Val Tyr Leu Glu Ser Leu
    370                 375                 380

Gln Asp Thr Lys Ile Thr Leu Ile Ile Asn Trp Leu Gln Glu Ala Leu
385                 390                 395                 400

Ser Ser Ala Ser Leu Ala His Met Lys Ala Lys Phe Arg Glu Thr Leu
                405                 410                 415

Glu Asp Thr Arg Asp Arg Met Tyr Gln Met Asp Ile Gln Gln Glu Leu
            420                 425                 430

Gln Arg Tyr Leu Ser Leu Val Gly Gln Val Tyr Ser Thr Leu Val Thr
        435                 440                 445

Tyr Ile Ser Asp Trp Trp Thr Leu Ala Ala Lys Asn Leu Thr Asp Phe
    450                 455                 460

Ala Glu Gln Tyr Ser Ile Gln Asp Trp Ala Lys Arg Met Lys Ala Leu
465                 470                 475                 480

Val Glu Gln Gly Phe Thr Val Pro Glu Ile Lys Thr Ile Leu Gly Thr
                485                 490                 495

Met Pro Ala Phe Glu Val Ser Leu Gln Ala Leu Gln Lys Ala Thr Phe
            500                 505                 510

Gln Thr Pro Asp Phe Ile Val Pro Leu Thr Asp Leu Arg Ile Pro Ser
        515                 520                 525

Val Gln Ile Asn Phe Lys Asp Leu Lys Asn Ile Lys Ile Pro Ser Arg
    530                 535                 540

Phe Ser Thr Pro Glu Phe Thr Ile Leu Asn Thr Phe His Ile Pro Ser
545                 550                 555                 560
```

```
Phe Thr Ile Asp Phe Val Glu Met Lys Val Lys Ile Ile Arg Thr Ile
            565                 570                 575

Asp Gln Met Gln Asn Ser Glu Leu Gln Trp Pro Val Pro Asp Ile Tyr
            580                 585                 590

Leu Arg Asp Leu Lys Val Glu Asp Ile Pro Leu Ala Arg Ile Thr Leu
            595                 600                 605

Pro Asp Phe Arg Leu Pro Glu Ile Ala Ile Pro Glu Phe Ile Ile Pro
610                 615                 620

Thr Leu Asn Leu Asn Asp Phe Gln Val Pro Asp Leu His Ile Pro Glu
625                 630                 635                 640

Phe Gln Leu Pro His Ile Ser His Thr Ile Glu Val Pro Thr Phe Gly
                    645                 650                 655

Lys Leu Tyr Ser Ile Leu Lys Ile Gln Ser Pro Leu Phe Thr Leu Asp
                    660                 665                 670

Ala Asn Ala Asp Ile Gly Asn Gly Thr Thr Ser Ala Asn Glu Ala Gly
                    675                 680                 685

Ile Ala Ala Ser Ile Thr Ala Lys Gly Glu Ser Lys Leu Glu Val Leu
690                 695                 700

Asn Phe Asp Phe Gln Ala Asn Ala Gln Leu Ser Asn Pro Lys Ile Asn
705                 710                 715                 720

Pro Leu Ala Leu Lys Glu Ser Val Lys Phe Ser Ser Lys Tyr Leu Arg
                    725                 730                 735

Thr Glu His Gly Ser Glu Met Leu Phe Phe Gly Asn Ala Ile Glu Gly
                    740                 745                 750

Lys Ser Asn Thr Val Ala Ser Leu His Thr Glu Lys Asn Thr Leu Glu
                    755                 760                 765

Leu Ser Asn Gly Val Ile Val Lys Ile Asn Asn Gln Leu Thr Leu Asp
                    770                 775                 780

Ser Asn Thr Lys Tyr Phe His Lys Leu Asn Ile Pro Lys Leu Asp Phe
785                 790                 795                 800

Ser Ser Gln Ala Asp Leu Arg Asn Glu Ile Lys Thr Leu Leu Lys Ala
                    805                 810                 815

Gly His Ile Ala Trp Thr Ser Ser Gly Lys Gly Ser Trp Lys Trp Ala
                    820                 825                 830

Cys Pro Arg Phe Ser Asp Glu Gly Thr His Glu Ser Gln Ile Ser Phe
                    835                 840                 845

Thr Ile Glu Gly Pro Leu Thr Ser Phe Gly Leu Ser Asn Lys Ile Asn
                    850                 855                 860

Ser Lys His Leu Arg Val Asn Gln Asn Leu Val Tyr Glu Ser Gly Ser
865                 870                 875                 880

Leu Asn Phe Ser Lys Leu Glu Ile Gln Ser Gln Val Asp Ser Gln His
                    885                 890                 895

Val Gly His Ser Val Leu Thr Ala Lys Gly Met Ala Leu Phe Gly Glu
                    900                 905                 910

Gly Lys Ala Glu Phe Thr Gly Arg His Asp Ala His Leu Asn Gly Lys
                    915                 920                 925

Val Ile Gly Thr Leu Lys Asn Ser Leu Phe Phe Ser Ala Gln Pro Phe
930                 935                 940

Glu Ile Thr Ala Ser Thr Asn Asn Glu Gly Asn Leu Lys Val Arg Phe
945                 950                 955                 960

Pro Leu Arg Leu Thr Gly Lys Ile Asp Phe Leu Asn Asn Tyr Ala Leu
                    965                 970                 975
```

```
Phe Leu Ser Pro Ser Ala Gln Gln Ala Ser Trp Gln Val Ser Ala Arg
            980                 985                 990

Phe Asn Gln Tyr Lys Tyr Asn Gln Asn Phe Ser Ala Gly Asn Asn Glu
            995                1000                1005

Asn Ile Met Glu Ala His Val Gly Ile Asn Gly Glu Ala Asn Leu
        1010                1015                1020

Asp Phe Leu Asn Ile Pro Leu Thr Ile Pro Glu Met Arg Leu Pro
        1025                1030                1035

Tyr Thr Ile Ile Thr Thr Pro Pro Leu Lys Asp Phe Ser Leu Trp
        1040                1045                1050

Glu Lys Thr Gly Leu Lys Glu Phe Leu Lys Thr Thr Lys Gln Ser
        1055                1060                1065

Phe Asp Leu Ser Val Lys Ala Gln Tyr Lys Lys Asn Lys His Arg
        1070                1075                1080

His Ser Ile Thr Asn Pro Leu Ala Val Leu Cys Glu Phe Ile Ser
        1085                1090                1095

Gln Ser Ile Lys Ser Phe Asp Arg His Phe Glu Lys Asn Arg Asn
        1100                1105                1110

Asn Ala Leu Asp Phe Val Thr Lys Ser Tyr Asn Glu Thr Lys Ile
        1115                1120                1125

Lys Phe Asp Lys Tyr Lys Ala Glu Lys Ser His Asp Glu Leu Pro
        1130                1135                1140

Arg Thr Phe Gln Ile Pro Gly Tyr Thr Val Pro Val Val Asn Val
        1145                1150                1155

Glu Val Ser Pro Phe Thr Ile Glu Met Ser Ala Phe Gly Tyr Val
        1160                1165                1170

Phe Pro Lys Ala Val Ser Met Pro Ser Phe Ser Ile Leu Gly Ser
        1175                1180                1185

Asp Val Arg Val Pro Ser Tyr Thr Leu Ile Leu Pro Ser Leu Glu
        1190                1195                1200

Leu Pro Val Leu His Val Pro Arg Asn Leu Lys Leu Ser Leu Pro
        1205                1210                1215

His Phe Lys Glu Leu Cys Thr Ile Ser His Ile Phe Ile Pro Ala
        1220                1225                1230

Met Gly Asn Ile Thr Tyr Asp Phe Ser Phe Lys Ser Ser Val Ile
        1235                1240                1245

Thr Leu Asn Thr Asn Ala Glu Leu Phe Asn Gln Ser Asp Ile Val
        1250                1255                1260

Ala His Leu Leu Ser Ser Ser Ser Ser Val Ile Asp Ala Leu Gln
        1265                1270                1275

Tyr Lys Leu Glu Gly Thr Thr Arg Leu Thr Arg Lys Arg Gly Leu
        1280                1285                1290

Lys Leu Ala Thr Ala Leu Ser Leu Ser Asn Lys Phe Val Glu Gly
        1295                1300                1305

Ser His Asn Ser Thr Val Ser Leu Thr Thr Lys Asn Met Glu Val
        1310                1315                1320

Ser Val Ala Lys Thr Thr Lys Ala Glu Ile Pro Ile Leu Arg Met
        1325                1330                1335

Asn Phe Lys Gln Glu Leu Asn Gly Asn Thr Lys Ser Lys Pro Thr
        1340                1345                1350

Val Ser Ser Ser Met Glu Phe Lys Tyr Asp Phe Asn Ser Ser Met
        1355                1360                1365
```

-continued

```
Leu Tyr Ser Thr Ala Lys Gly Ala Val Asp His Lys Leu Ser Leu
    1370            1375            1380

Glu Ser Leu Thr Ser Tyr Phe Ser Ile Glu Ser Ser Thr Lys Gly
    1385            1390            1395

Asp Val Lys Gly Ser Val Leu Ser Arg Glu Tyr Ser Gly Thr Ile
    1400            1405            1410

Ala Ser Glu Ala Asn Thr Tyr Leu Asn Ser Lys Ser Thr Arg Ser
    1415            1420            1425

Ser Val Lys Leu Gln Gly Thr Ser Lys Ile Asp Asp Ile Trp Asn
    1430            1435            1440

Leu Glu Val Lys Glu Asn Phe Ala Gly Glu Ala Thr Leu Gln Arg
    1445            1450            1455

Ile Tyr Ser Leu Trp Glu His Ser Thr Lys Asn His Leu Gln Leu
    1460            1465            1470

Glu Gly Leu Phe Phe Thr Asn Gly Glu His Thr Ser Lys Ala Thr
    1475            1480            1485

Leu Glu Leu Ser Pro Trp Gln Met Ser Ala Leu Val Gln Val His
    1490            1495            1500

Ala Ser Gln Pro Ser Ser Phe His Asp Phe Pro Asp Leu Gly Gln
    1505            1510            1515

Glu Val Ala Leu Asn Ala Asn Thr Lys Asn Gln Lys Ile Arg Trp
    1520            1525            1530

Lys Asn Glu Val Arg Ile His Ser Gly Ser Phe Gln Ser Gln Val
    1535            1540            1545

Glu Leu Ser Asn Asp Gln Glu Lys Ala His Leu Asp Ile Ala Gly
    1550            1555            1560

Ser Leu Glu Gly His Leu Arg Phe Leu Lys Asn Ile Ile Leu Pro
    1565            1570            1575

Val Tyr Asp Lys Ser Leu Trp Asp Phe Leu Lys Leu Asp Val Thr
    1580            1585            1590

Thr Ser Ile Gly Arg Arg Gln His Leu Arg Val Ser Thr Ala Phe
    1595            1600            1605

Val Tyr Thr Lys Asn Pro Asn Gly Tyr Ser Phe Ser Ile Pro Val
    1610            1615            1620

Lys Val Leu Ala Asp Lys Phe Ile Thr Pro Gly Leu Lys Leu Asn
    1625            1630            1635

Asp Leu Asn Ser Val Leu Val Met Pro Thr Phe His Val Pro Phe
    1640            1645            1650

Thr Asp Leu Gln Val Pro Ser Cys Lys Leu Asp Phe Arg Glu Ile
    1655            1660            1665

Gln Ile Tyr Lys Lys Leu Arg Thr Ser Ser Phe Ala Leu Asn Leu
    1670            1675            1680

Pro Thr Leu Pro Glu Val Lys Phe Pro Glu Val Asp Val Leu Thr
    1685            1690            1695

Lys Tyr Ser Gln Pro Glu Asp Ser Leu Ile Pro Phe Phe Glu Ile
    1700            1705            1710

Thr Val Pro Glu Ser Gln Leu Thr Val Ser Gln Phe Thr Leu Pro
    1715            1720            1725

Lys Ser Val Ser Asp Gly Ile Ala Ala Leu Asp Leu Asn Ala Val
    1730            1735            1740

Ala Asn Lys Ile Ala Asp Phe Glu Leu Pro Thr Ile Ile Val Pro
    1745            1750            1755
```

-continued

| | | | | | | | | | | |
|---|---|---|---|---|---|---|---|---|---|---|
| Glu | Gln | Thr | Ile | Glu | Ile | Pro | Ser | Ile | Lys | Phe | Ser | Val | Pro | Ala |
| 1760 | | | | | 1765 | | | | | 1770 | | | | |

Glu Gln Thr Ile Glu Ile Pro Ser Ile Lys Phe Ser Val Pro Ala
1760                    1765                    1770

Gly Ile Val Ile Pro Ser Phe Gln Ala Leu Thr Ala Arg Phe Glu
1775                    1780                    1785

Val Asp Ser Pro Val Tyr Asn Ala Thr Trp Ser Ala Ser Leu Lys
1790                    1795                    1800

Asn Lys Ala Asp Tyr Val Glu Thr Val Leu Asp Ser Thr Cys Ser
1805                    1810                    1815

Ser Thr Val Gln Phe Leu Glu Tyr Glu Leu Asn Val Leu Gly Thr
1820                    1825                    1830

His Lys Ile Glu Asp Gly Thr Leu Ala Ser Lys Thr Lys Gly Thr
1835                    1840                    1845

Leu Ala His Arg Asp Phe Ser Ala Glu Tyr Glu Glu Asp Gly Lys
1850                    1855                    1860

Phe Glu Gly Leu Gln Glu Trp Glu Gly Lys Ala His Leu Asn Ile
1865                    1870                    1875

Lys Ser Pro Ala Phe Thr Asp Leu His Leu Arg Tyr Gln Lys Asp
1880                    1885                    1890

Lys Lys Gly Ile Ser Thr Ser Ala Ala Ser Pro Ala Val Gly Thr
1895                    1900                    1905

Val Gly Met Asp Met Asp Glu Asp Asp Asp Phe Ser Lys Trp Asn
1910                    1915                    1920

Phe Tyr Tyr Ser Pro Gln Ser Ser Pro Asp Lys Lys Leu Thr Ile
1925                    1930                    1935

Phe Lys Thr Glu Leu Arg Val Arg Glu Ser Asp Glu Glu Thr Gln
1940                    1945                    1950

Ile Lys Val Asn Trp Glu Glu Glu Ala Ala Ser Gly Leu Leu Thr
1955                    1960                    1965

Ser Leu Lys Asp Asn Val Pro Lys Ala Thr Gly Val Leu Tyr Asp
1970                    1975                    1980

Tyr Val Asn Lys Tyr His Trp Glu His Thr Gly Leu Thr Leu Arg
1985                    1990                    1995

Glu Val Ser Ser Lys Leu Arg Arg Asn Leu Gln Asn Asn Ala Glu
2000                    2005                    2010

Trp Val Tyr Gln Gly Ala Ile Arg Gln Ile Asp Asp Ile Asp Val
2015                    2020                    2025

Arg Phe Gln Lys Ala Ala Ser Gly Thr Thr Gly Thr Tyr Gln Glu
2030                    2035                    2040

Trp Lys Asp Lys Ala Gln Asn Leu Tyr Gln Glu Leu Leu Thr Gln
2045                    2050                    2055

Glu Gly Gln Ala Ser Phe Gln Gly Leu Lys Asp Asn Val Phe Asp
2060                    2065                    2070

Gly Leu Val Arg Val Thr Gln Lys Phe His Met Lys Val Lys His
2075                    2080                    2085

Leu Ile Asp Ser Leu Ile Asp Phe Leu Asn Phe Pro Arg Phe Gln
2090                    2095                    2100

Phe Pro Gly Lys Pro Gly Ile Tyr Thr Arg Glu Glu Leu Cys Thr
2105                    2110                    2115

Met Phe Ile Arg Glu Val Gly Thr Val Leu Ser Gln Val Tyr Ser
2120                    2125                    2130

Lys Val His Asn Gly Ser Glu Ile Leu Phe Ser Tyr Phe Gln Asp
2135                    2140                    2145

```
Leu Val Ile Thr Leu Pro Phe Glu Leu Arg Lys His Lys Leu Ile
    2150            2155                2160
Asp Val Ile Ser Met Tyr Arg Glu Leu Leu Lys Asp Leu Ser Lys
    2165            2170                2175
Glu Ala Gln Glu Val Phe Lys Ala Ile Gln Ser Leu Lys Thr Thr
    2180            2185                2190
Glu Val Leu Arg Asn Leu Gln Asp Leu Leu Gln Phe Ile Phe Gln
    2195            2200                2205
Leu Ile Glu Asp Asn Ile Lys Gln Leu Lys Glu Met Lys Phe Thr
    2210            2215                2220
Tyr Leu Ile Asn Tyr Ile Gln Asp Glu Ile Asn Thr Ile Phe Asn
    2225            2230                2235
Asp Tyr Ile Pro Tyr Val Phe Lys Leu Leu Lys Glu Asn Leu Cys
    2240            2245                2250
Leu Asn Leu His Lys Phe Asn Glu Phe Ile Gln Asn Glu Leu Gln
    2255            2260                2265
Glu Ala Ser Gln Glu Leu Gln Gln Ile His Gln Tyr Ile Met Ala
    2270            2275                2280
Leu Arg Glu Glu Tyr Phe Asp Pro Ser Ile Val Gly Trp Thr Val
    2285            2290                2295
Lys Tyr Tyr Glu Leu Glu Glu Lys Ile Val Ser Leu Ile Lys Asn
    2300            2305                2310
Leu Leu Val Ala Leu Lys Asp Phe His Ser Glu Tyr Ile Val Ser
    2315            2320                2325
Ala Ser Asn Phe Thr Ser Gln Leu Ser Ser Gln Val Glu Gln Phe
    2330            2335                2340
Leu His Arg Asn Ile Gln Glu Tyr Leu Ser Ile Leu Thr Asp Pro
    2345            2350                2355
Asp Gly Lys Gly Lys Glu Lys Ile Ala Glu Leu Ser Ala Thr Ala
    2360            2365                2370
Gln Glu Ile Ile Lys Ser Gln Ala Ile Ala Thr Lys Lys Ile Ile
    2375            2380                2385
Ser Asp Tyr His Gln Gln Phe Arg Tyr Lys Leu Gln Asp Phe Ser
    2390            2395                2400
Asp Gln Leu Ser Asp Tyr Tyr Glu Lys Phe Ile Ala Glu Ser Lys
    2405            2410                2415
Arg Leu Ile Asp Leu Ser Ile Gln Asn Tyr His Thr Phe Leu Ile
    2420            2425                2430
Tyr Ile Thr Glu Leu Leu Lys Lys Leu Gln Ser Thr Thr Val Met
    2435            2440                2445
Asn Pro Tyr Met Lys Leu Ala Pro Gly Glu Leu Thr Ile Ile Leu
    2450            2455                2460

<210> SEQ ID NO 5
<211> LENGTH: 474
<212> TYPE: PRT
<213> ORGANISM: Homo sapiens

<400> SEQUENCE: 5

Met Lys Arg Val Leu Val Leu Leu Ala Val Ala Phe Gly His Ala
1               5                   10                  15

Leu Glu Arg Gly Arg Asp Tyr Glu Lys Asn Lys Val Cys Lys Glu Phe
                20                  25                  30

Ser His Leu Gly Lys Glu Asp Phe Thr Ser Leu Ser Leu Val Leu Tyr
                35                  40                  45
```

-continued

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
 65                  70                  75                  80

Pro Asp Cys Tyr Asp Thr Arg Thr Ser Ala Leu Ser Ala Lys Ser Cys
                     85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Glu Gln Ala Pro Leu Ser Leu Leu Val
                    165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                    245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Arg Leu Pro Thr Asn Lys Asp Val Cys Asp
                    325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
    370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                    405                 410                 415

Glu Tyr Lys Lys Lys Leu Ala Glu Arg Leu Lys Ala Lys Leu Pro Glu
            420                 425                 430

Ala Thr Pro Thr Glu Leu Ala Lys Leu Val Asn Lys Arg Ser Asp Phe
        435                 440                 445

```
Ala Ser Asn Cys Cys Ser Ile Asn Ser Pro Pro Leu Tyr Cys Asp Ser
    450                 455                 460

Glu Ile Asp Ala Glu Leu Lys Asn Ile Leu
465                 470
```

<210> SEQ ID NO 6
<211> LENGTH: 474
<212> TYPE: PRT
<213> ORGANISM: Homo sapiens

<400> SEQUENCE: 6

```
Met Lys Arg Val Leu Val Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350
```

```
Arg Thr His Leu Pro Glu Val Phe Leu Ser Lys Val Leu Glu Pro Thr
            355                 360                 365

Leu Lys Ser Leu Gly Glu Cys Cys Asp Val Glu Asp Ser Thr Thr Cys
370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Glu
                420                 425                 430

Ala Thr Pro Thr Glu Leu Ala Lys Leu Val Asn Lys Arg Ser Asp Phe
            435                 440                 445

Ala Ser Asn Cys Cys Ser Ile Asn Ser Pro Pro Leu Tyr Cys Asp Ser
450                 455                 460

Glu Ile Asp Ala Glu Leu Lys Asn Ile Leu
465                 470

<210> SEQ ID NO 7
<211> LENGTH: 318
<212> TYPE: PRT
<213> ORGANISM: Homo sapiens

<400> SEQUENCE: 7

Met Ala Ser Pro Gly Cys Leu Leu Cys Val Leu Gly Leu Leu Leu Cys
1               5                   10                  15

Gly Ala Ala Ser Leu Glu Leu Ser Arg Pro His Gly Asp Thr Ala Lys
            20                  25                  30

Lys Pro Ile Ile Gly Ile Leu Met Gln Lys Cys Arg Asn Lys Val Met
            35                  40                  45

Lys Asn Tyr Gly Arg Tyr Tyr Ile Ala Ala Ser Tyr Val Lys Tyr Leu
        50                  55                  60

Glu Ser Ala Gly Ala Arg Val Val Pro Val Arg Leu Asp Leu Thr Glu
65                  70                  75                  80

Lys Asp Tyr Glu Ile Leu Phe Lys Ser Ile Asn Gly Ile Leu Phe Pro
                85                  90                  95

Gly Gly Ser Val Asp Leu Arg Arg Ser Asp Tyr Ala Lys Val Ala Lys
            100                 105                 110

Ile Phe Tyr Asn Leu Ser Ile Gln Ser Phe Asp Asp Gly Asp Tyr Phe
        115                 120                 125

Pro Val Trp Gly Thr Cys Leu Gly Phe Glu Glu Leu Ser Leu Leu Ile
    130                 135                 140

Ser Gly Glu Cys Leu Leu Thr Ala Thr Asp Thr Val Asp Val Ala Met
145                 150                 155                 160

Pro Leu Asn Phe Thr Gly Gly Gln Leu His Ser Arg Met Phe Gln Asn
                165                 170                 175

Phe Pro Thr Glu Leu Leu Leu Ser Leu Ala Val Glu Pro Leu Thr Ala
            180                 185                 190

Asn Phe His Lys Trp Ser Leu Ser Val Lys Asn Phe Thr Met Asn Glu
        195                 200                 205

Lys Leu Lys Lys Phe Phe Asn Val Leu Thr Thr Asn Thr Asp Gly Lys
    210                 215                 220

Ile Glu Phe Ile Ser Thr Met Glu Gly Tyr Lys Tyr Pro Val Tyr Gly
225                 230                 235                 240

Val Gln Trp His Pro Glu Lys Ala Pro Tyr Glu Trp Lys Asn Leu Asp
                245                 250                 255
```

```
Gly Ile Ser His Ala Pro Asn Ala Val Lys Thr Ala Phe Tyr Leu Ala
            260                 265                 270

Glu Phe Phe Val Asn Glu Ala Arg Lys Asn Asn His His Phe Lys Ser
        275                 280                 285

Glu Ser Glu Glu Lys Ala Leu Ile Tyr Gln Phe Ser Pro Ile Tyr
    290                 295                 300

Thr Gly Asn Ile Ser Ser Phe Gln Gln Cys Tyr Ile Phe Asp
305                 310                 315

<210> SEQ ID NO 8
<211> LENGTH: 709
<212> TYPE: PRT
<213> ORGANISM: Homo sapiens

<400> SEQUENCE: 8

Met Ala Thr Ala Gly Gly Ser Gly Ala Asp Pro Gly Ser Arg Gly
1               5                   10                  15

Leu Leu Arg Leu Leu Ser Phe Cys Val Leu Leu Ala Gly Leu Cys Arg
                20                  25                  30

Gly Asn Ser Val Glu Arg Lys Ile Tyr Ile Pro Leu Asn Lys Thr Ala
            35                  40                  45

Pro Cys Val Arg Leu Leu Asn Ala Thr His Gln Ile Gly Cys Gln Ser
        50                  55                  60

Ser Ile Ser Gly Asp Thr Gly Val Ile His Val Glu Lys Glu Glu
65                  70                  75                  80

Asp Leu Gln Trp Val Leu Thr Asp Gly Pro Asn Pro Tyr Met Val
                85                  90                  95

Leu Leu Glu Ser Lys His Phe Thr Arg Asp Leu Met Glu Lys Leu Lys
                100                 105                 110

Gly Arg Thr Ser Arg Ile Ala Gly Leu Ala Val Ser Leu Thr Lys Pro
            115                 120                 125

Ser Pro Ala Ser Gly Phe Ser Pro Ser Val Gln Cys Pro Asn Asp Gly
        130                 135                 140

Phe Gly Val Tyr Ser Asn Ser Tyr Gly Pro Glu Phe Ala His Cys Arg
145                 150                 155                 160

Glu Ile Gln Trp Asn Ser Leu Gly Asn Gly Leu Ala Tyr Glu Asp Phe
                165                 170                 175

Ser Phe Pro Ile Phe Leu Leu Glu Asp Glu Asn Glu Thr Lys Val Ile
            180                 185                 190

Lys Gln Cys Tyr Gln Asp His Asn Leu Ser Gln Asn Gly Ser Ala Pro
        195                 200                 205

Thr Phe Pro Leu Cys Ala Met Gln Leu Phe Ser His Met His Ala Val
    210                 215                 220

Ile Ser Thr Ala Thr Cys Met Arg Arg Ser Ser Ile Gln Ser Thr Phe
225                 230                 235                 240

Ser Ile Asn Pro Glu Ile Val Cys Asp Pro Leu Ser Asp Tyr Asn Val
                245                 250                 255

Trp Ser Met Leu Lys Pro Ile Asn Thr Thr Gly Thr Leu Lys Pro Asp
            260                 265                 270

Asp Arg Val Val Val Ala Ala Thr Arg Leu Asp Ser Arg Ser Phe Phe
        275                 280                 285

Trp Asn Val Ala Pro Gly Ala Glu Ser Ala Val Ala Ser Phe Val Thr
    290                 295                 300
```

```
Gln Leu Ala Ala Ala Glu Ala Leu Gln Lys Ala Pro Asp Val Thr Thr
305                 310                 315                 320

Leu Pro Arg Asn Val Met Phe Val Phe Phe Gln Gly Glu Thr Phe Asp
            325                 330                 335

Tyr Ile Gly Ser Ser Arg Met Val Tyr Asp Met Glu Lys Gly Lys Phe
        340                 345                 350

Pro Val Gln Leu Glu Asn Val Asp Ser Phe Val Glu Leu Gly Gln Val
    355                 360                 365

Ala Leu Arg Thr Ser Leu Glu Leu Trp Met His Thr Asp Pro Val Ser
370                 375                 380

Gln Lys Asn Glu Ser Val Arg Asn Gln Val Glu Asp Leu Leu Ala Thr
385                 390                 395                 400

Leu Glu Lys Ser Gly Ala Gly Val Pro Ala Val Ile Leu Arg Arg Pro
                405                 410                 415

Asn Gln Ser Gln Pro Leu Pro Pro Ser Ser Leu Gln Arg Phe Leu Arg
            420                 425                 430

Ala Arg Asn Ile Ser Gly Val Val Leu Ala Asp His Ser Gly Ala Phe
        435                 440                 445

His Asn Lys Tyr Tyr Gln Ser Ile Tyr Asp Thr Ala Glu Asn Ile Asn
    450                 455                 460

Val Ser Tyr Pro Glu Trp Leu Ser Pro Glu Glu Asp Leu Asn Phe Val
465                 470                 475                 480

Thr Asp Thr Ala Lys Ala Leu Ala Asp Val Ala Thr Val Leu Gly Arg
                485                 490                 495

Ala Leu Tyr Glu Leu Ala Gly Gly Thr Asn Phe Ser Asp Thr Val Gln
            500                 505                 510

Ala Asp Pro Gln Thr Val Thr Arg Leu Leu Tyr Gly Phe Leu Ile Lys
        515                 520                 525

Ala Asn Asn Ser Trp Phe Gln Ser Ile Leu Arg Gln Asp Leu Arg Ser
    530                 535                 540

Tyr Leu Gly Asp Gly Pro Leu Gln His Tyr Ile Ala Val Ser Ser Pro
545                 550                 555                 560

Thr Asn Thr Thr Tyr Val Val Gln Tyr Ala Leu Ala Asn Leu Thr Gly
                565                 570                 575

Thr Val Val Asn Leu Thr Arg Glu Gln Cys Gln Asp Pro Ser Lys Val
            580                 585                 590

Pro Ser Glu Asn Lys Asp Leu Tyr Glu Tyr Ser Trp Val Gln Gly Pro
    595                 600                 605

Leu His Ser Asn Glu Thr Asp Arg Leu Pro Arg Cys Val Arg Ser Thr
610                 615                 620

Ala Arg Leu Ala Arg Ala Leu Ser Pro Ala Phe Glu Leu Ser Gln Trp
625                 630                 635                 640

Ser Ser Thr Glu Tyr Ser Thr Trp Thr Glu Ser Arg Trp Lys Asp Ile
                645                 650                 655

Arg Ala Arg Ile Phe Leu Ile Ala Ser Lys Glu Leu Glu Leu Ile Thr
            660                 665                 670

Leu Thr Val Gly Phe Gly Ile Leu Ile Phe Ser Leu Ile Val Thr Tyr
        675                 680                 685

Cys Ile Asn Ala Lys Ala Asp Val Leu Phe Ile Ala Pro Arg Glu Pro
    690                 695                 700

Gly Ala Val Ser Tyr
705
```

<210> SEQ ID NO 9
<211> LENGTH: 347
<212> TYPE: PRT
<213> ORGANISM: Homo sapiens

<400> SEQUENCE: 9

```
Met Ala Gln Ser Arg Asp Gly Gly Asn Pro Phe Ala Glu Pro Ser Glu
 1               5                  10                  15

Leu Asp Asn Pro Phe Gln Asp Pro Ala Val Ile Gln His Arg Pro Ser
             20                  25                  30

Arg Gln Tyr Ala Thr Leu Asp Val Tyr Asn Pro Phe Glu Thr Arg Glu
         35                  40                  45

Pro Pro Pro Ala Tyr Glu Pro Pro Ala Pro Ala Pro Leu Pro Pro Pro
     50                  55                  60

Ser Ala Pro Ser Leu Gln Pro Ser Arg Lys Leu Ser Pro Thr Glu Pro
 65                  70                  75                  80

Lys Asn Tyr Gly Ser Tyr Ser Thr Gln Ala Ser Ala Ala Ala Ala Thr
                 85                  90                  95

Ala Glu Leu Leu Lys Lys Gln Glu Glu Leu Asn Arg Lys Ala Glu Glu
            100                 105                 110

Leu Asp Arg Arg Glu Arg Glu Leu Gln His Ala Ala Leu Gly Gly Thr
        115                 120                 125

Ala Thr Arg Gln Asn Asn Trp Pro Pro Leu Pro Ser Phe Cys Pro Val
    130                 135                 140

Gln Pro Cys Phe Phe Gln Asp Ile Ser Met Glu Ile Pro Gln Glu Phe
145                 150                 155                 160

Gln Lys Thr Val Ser Thr Met Tyr Tyr Leu Trp Met Cys Ser Thr Leu
                165                 170                 175

Ala Leu Leu Leu Asn Phe Leu Ala Cys Leu Ala Ser Phe Cys Val Glu
            180                 185                 190

Thr Asn Asn Gly Ala Gly Phe Gly Leu Ser Ile Leu Trp Val Leu Leu
        195                 200                 205

Phe Thr Pro Cys Ser Phe Val Cys Trp Tyr Arg Pro Met Tyr Lys Ala
    210                 215                 220

Phe Arg Ser Asp Ser Ser Phe Asn Phe Phe Val Phe Phe Phe Ile Phe
225                 230                 235                 240

Phe Val Gln Asp Val Leu Phe Val Leu Gln Ala Ile Gly Ile Pro Gly
                245                 250                 255

Trp Gly Phe Ser Gly Trp Ile Ser Ala Leu Val Val Pro Lys Gly Asn
            260                 265                 270

Thr Ala Val Ser Val Leu Met Leu Leu Val Ala Leu Leu Phe Thr Gly
        275                 280                 285

Ile Ala Val Leu Gly Ile Val Met Leu Lys Arg Ile His Ser Leu Tyr
    290                 295                 300

Arg Arg Thr Gly Ala Ser Phe Gln Lys Ala Gln Gln Glu Phe Ala Ala
305                 310                 315                 320

Gly Val Phe Ser Asn Pro Ala Val Arg Thr Ala Ala Ala Asn Ala Ala
                325                 330                 335

Ala Gly Ala Ala Glu Asn Ala Phe Arg Ala Pro
            340                 345
```

<210> SEQ ID NO 10
<211> LENGTH: 321
<212> TYPE: PRT
<213> ORGANISM: Homo sapiens

```
<400> SEQUENCE: 10

Met Ala Gln Ser Arg Asp Gly Gly Asn Pro Phe Ala Glu Pro Ser Glu
1               5                   10                  15

Leu Asp Asn Pro Phe Gln Pro Pro Ala Tyr Glu Pro Pro Ala Pro
            20                  25                  30

Ala Pro Leu Pro Pro Ser Ala Pro Ser Leu Gln Pro Ser Arg Lys
        35                  40                  45

Leu Ser Pro Thr Glu Pro Lys Asn Tyr Gly Ser Tyr Ser Thr Gln Ala
    50                  55                  60

Ser Ala Ala Ala Thr Ala Glu Leu Leu Lys Lys Gln Glu Glu Leu
65                  70                  75                  80

Asn Arg Lys Ala Glu Glu Leu Asp Arg Arg Glu Arg Glu Leu Gln His
                85                  90                  95

Ala Ala Leu Gly Gly Thr Ala Thr Arg Gln Asn Asn Trp Pro Pro Leu
                100                 105                 110

Pro Ser Phe Cys Pro Val Gln Pro Cys Phe Phe Gln Asp Ile Ser Met
        115                 120                 125

Glu Ile Pro Gln Glu Phe Gln Lys Thr Val Ser Thr Met Tyr Tyr Leu
130                 135                 140

Trp Met Cys Ser Thr Leu Ala Leu Leu Leu Asn Phe Leu Ala Cys Leu
145                 150                 155                 160

Ala Ser Phe Cys Val Glu Thr Asn Asn Gly Ala Gly Phe Gly Leu Ser
                165                 170                 175

Ile Leu Trp Val Leu Leu Phe Thr Pro Cys Ser Phe Val Cys Trp Tyr
            180                 185                 190

Arg Pro Met Tyr Lys Ala Phe Arg Ser Asp Ser Ser Phe Asn Phe Phe
            195                 200                 205

Val Phe Phe Phe Ile Phe Phe Val Gln Asp Val Leu Phe Val Leu Gln
            210                 215                 220

Ala Ile Gly Ile Pro Gly Trp Gly Phe Ser Gly Trp Ile Ser Ala Leu
225                 230                 235                 240

Val Val Pro Lys Gly Asn Thr Ala Val Ser Val Leu Met Leu Leu Val
                245                 250                 255

Ala Leu Leu Phe Thr Gly Ile Ala Val Leu Gly Ile Val Met Leu Lys
                260                 265                 270

Arg Ile His Ser Leu Tyr Arg Arg Thr Gly Ala Ser Phe Gln Lys Ala
            275                 280                 285

Gln Gln Glu Phe Ala Ala Gly Val Phe Ser Asn Pro Ala Val Arg Thr
        290                 295                 300

Ala Ala Ala Asn Ala Ala Ala Gly Ala Ala Glu Asn Ala Phe Arg Ala
305                 310                 315                 320

Pro

<210> SEQ ID NO 11
<211> LENGTH: 541
<212> TYPE: PRT
<213> ORGANISM: Homo sapiens

<400> SEQUENCE: 11

Met Lys Phe Leu Ile Phe Ala Phe Phe Gly Gly Val His Leu Leu Ser
1               5                   10                  15

Leu Cys Ser Gly Lys Ala Ile Cys Lys Asn Gly Ile Ser Lys Arg Thr
            20                  25                  30
```

-continued

Phe Glu Glu Ile Lys Glu Ile Ala Ser Cys Gly Asp Val Ala Lys
       35                  40                  45

Ala Ile Ile Asn Leu Ala Val Tyr Gly Lys Ala Gln Asn Arg Ser Tyr
        50                  55                  60

Glu Arg Leu Ala Leu Leu Val Asp Thr Val Gly Pro Arg Leu Ser Gly
65                  70                  75                  80

Ser Lys Asn Leu Glu Lys Ala Ile Gln Ile Met Tyr Gln Asn Leu Gln
                    85                  90                  95

Gln Asp Gly Leu Glu Lys Val His Leu Glu Pro Val Arg Ile Pro His
            100                 105                 110

Trp Glu Arg Gly Glu Ser Ala Val Met Leu Glu Pro Arg Ile His
            115                 120                 125

Lys Ile Ala Ile Leu Gly Leu Gly Ser Ser Ile Gly Thr Pro Pro Glu
    130                 135                 140

Gly Ile Thr Ala Glu Val Leu Val Val Thr Ser Phe Asp Glu Leu Gln
145                 150                 155                 160

Arg Arg Ala Ser Glu Ala Arg Gly Lys Ile Val Val Tyr Asn Gln Pro
                165                 170                 175

Tyr Ile Asn Tyr Ser Arg Thr Val Gln Tyr Arg Thr Gln Gly Ala Val
            180                 185                 190

Glu Ala Ala Lys Val Gly Ala Leu Ala Ser Leu Ile Arg Ser Val Ala
            195                 200                 205

Ser Phe Ser Ile Tyr Ser Pro His Thr Gly Ile Gln Glu Tyr Gln Asp
    210                 215                 220

Gly Val Pro Lys Ile Pro Thr Ala Cys Ile Thr Val Glu Asp Ala Glu
225                 230                 235                 240

Met Met Ser Arg Met Ala Ser His Gly Ile Lys Ile Val Ile Gln Leu
                245                 250                 255

Lys Met Gly Ala Lys Thr Tyr Pro Asp Thr Asp Ser Phe Asn Thr Val
            260                 265                 270

Ala Glu Ile Thr Gly Ser Lys Tyr Pro Glu Gln Val Val Leu Val Ser
            275                 280                 285

Gly His Leu Asp Ser Trp Asp Val Gly Gln Gly Ala Met Asp Asp Gly
    290                 295                 300

Gly Gly Ala Phe Ile Ser Trp Glu Ala Leu Ser Leu Ile Lys Asp Leu
305                 310                 315                 320

Gly Leu Arg Pro Lys Arg Thr Leu Arg Leu Val Leu Trp Thr Ala Glu
                325                 330                 335

Glu Gln Gly Gly Val Gly Ala Phe Gln Tyr Tyr Gln Leu His Lys Val
            340                 345                 350

Asn Ile Ser Asn Tyr Ser Leu Val Met Glu Ser Asp Ala Gly Thr Phe
            355                 360                 365

Leu Pro Thr Gly Leu Gln Phe Thr Gly Ser Gly Lys Ala Arg Ala Ile
    370                 375                 380

Met Glu Glu Val Met Ser Leu Leu Gln Pro Leu Asn Ile Thr Gln Val
385                 390                 395                 400

Leu Ser His Gly Glu Gly Thr Asp Ile Asn Phe Trp Ile Gln Ala Gly
                405                 410                 415

Val Pro Gly Ala Ser Leu Leu Asp Asp Leu Tyr Lys Tyr Phe Phe Phe
            420                 425                 430

His His Ser His Gly Asp Thr Met Thr Val Met Asp Pro Ser Arg Trp
    435                 440                 445

```
Met Leu Leu Leu Leu Phe Gly Leu Leu Phe Leu Met Leu Leu Gln Thr
            450                 455                 460
Trp Lys Lys Cys Cys Leu Gly Pro Arg Asn Ser Lys Lys Glu Thr Phe
465                 470                 475                 480
Ser Cys Phe Trp Pro Gly Ile Leu Gly Leu Gln Leu Trp Lys Thr Pro
                    485                 490                 495
Leu His Ile Thr Ile Ser Ser Asn Ser Ser Lys His Asn Ser Ile
                500                 505                 510
Ser Cys Phe Leu Leu Leu Ser Phe Leu Ile Leu Ser Lys Phe Ser Asp
                515                 520                 525
Ser Arg Lys Arg Asn His Ser Pro Leu Pro Pro Thr Thr
530                 535                 540
```

```
<210> SEQ ID NO 12
<211> LENGTH: 441
<212> TYPE: PRT
<213> ORGANISM: Homo sapiens

<400> SEQUENCE: 12

Met Val Pro Pro Lys Leu His Val Leu Phe Cys Leu Cys Gly Cys Leu
1               5                   10                  15
Ala Val Val Tyr Pro Phe Asp Trp Gln Tyr Ile Asn Pro Val Ala His
                20                  25                  30
Met Lys Ser Ser Ala Trp Val Asn Lys Ile Gln Val Leu Met Ala Ala
            35                  40                  45
Ala Ser Phe Gly Gln Thr Lys Ile Pro Arg Gly Asn Gly Pro Tyr Ser
        50                  55                  60
Val Gly Cys Thr Asp Leu Met Phe Asp His Thr Asn Lys Gly Thr Phe
65                  70                  75                  80
Leu Arg Leu Tyr Tyr Pro Ser Gln Asp Asn Asp Arg Leu Asp Thr Leu
                85                  90                  95
Trp Ile Pro Asn Lys Glu Tyr Phe Trp Gly Leu Ser Lys Phe Leu Gly
                100                 105                 110
Thr His Trp Leu Met Gly Asn Ile Leu Arg Leu Leu Phe Gly Ser Met
            115                 120                 125
Thr Thr Pro Ala Asn Trp Asn Ser Pro Leu Arg Pro Gly Glu Lys Tyr
        130                 135                 140
Pro Leu Val Val Phe Ser His Gly Leu Gly Ala Phe Arg Thr Leu Tyr
145                 150                 155                 160
Ser Ala Ile Gly Ile Asp Leu Ala Ser His Gly Phe Ile Val Ala Ala
                165                 170                 175
Val Glu His Arg Asp Arg Ser Ala Ser Ala Thr Tyr Tyr Phe Lys Asp
                180                 185                 190
Gln Ser Ala Ala Glu Ile Gly Asp Lys Ser Trp Leu Tyr Leu Arg Thr
            195                 200                 205
Leu Lys Gln Glu Glu Glu Thr His Ile Arg Asn Gln Gln Val Arg Gln
        210                 215                 220
Arg Ala Lys Glu Cys Ser Gln Ala Leu Ser Leu Ile Leu Asp Ile Asp
225                 230                 235                 240
His Gly Lys Pro Val Lys Asn Ala Leu Asp Leu Lys Phe Asp Met Glu
                245                 250                 255
Gln Leu Lys Asp Ser Ile Asp Arg Glu Lys Ile Ala Val Ile Gly His
            260                 265                 270
Ser Phe Gly Gly Ala Thr Val Ile Gln Thr Leu Ser Glu Asp Gln Arg
        275                 280                 285
```

```
Phe Arg Cys Gly Ile Ala Leu Asp Ala Trp Met Phe Pro Leu Gly Asp
        290                 295                 300

Glu Val Tyr Ser Arg Ile Pro Gln Pro Leu Phe Ile Asn Ser Glu
305                 310                 315                 320

Tyr Phe Gln Tyr Pro Ala Asn Ile Ile Lys Met Lys Lys Cys Tyr Ser
                325                 330                 335

Pro Asp Lys Glu Arg Lys Met Ile Thr Ile Arg Gly Ser Val His Gln
            340                 345                 350

Asn Phe Ala Asp Phe Thr Phe Ala Thr Gly Lys Ile Ile Gly His Met
        355                 360                 365

Leu Lys Leu Lys Gly Asp Ile Asp Ser Asn Val Ala Ile Asp Leu Ser
    370                 375                 380

Asn Lys Ala Ser Leu Ala Phe Leu Gln Lys His Leu Gly Leu His Lys
385                 390                 395                 400

Asp Phe Asp Gln Trp Asp Cys Leu Ile Glu Gly Asp Glu Asn Leu
                405                 410                 415

Ile Pro Gly Thr Asn Ile Asn Thr Thr Asn Gln His Ile Met Leu Gln
            420                 425                 430

Asn Ser Ser Gly Ile Glu Lys Tyr Asn
            435                 440

<210> SEQ ID NO 13
<211> LENGTH: 212
<212> TYPE: PRT
<213> ORGANISM: Homo sapiens

<400> SEQUENCE: 13

Met Met Gly Ile Pro Ile Arg Lys Phe Ile Cys Ala Ser Asn Gln Asn
1               5                   10                  15

His Val Leu Thr Asp Phe Ile Lys Thr Gly His Tyr Asp Leu Arg Glu
            20                  25                  30

Arg Lys Leu Ala Gln Thr Phe Ser Pro Ser Ile Asp Ile Leu Lys Ser
        35                  40                  45

Ser Asn Leu Glu Arg His Leu His Leu Met Ala Asn Asn Arg Leu Glu
    50                  55                  60

Ser Gln His His Phe Gln Ile Glu Lys Ala Leu Val Glu Lys Leu Gln
65                  70                  75                  80

Gln Asp Phe Val Ala Asp Trp Cys Ser Glu Gly Cys Leu Ala Ala
                85                  90                  95

Ile Asn Ser Thr Tyr Asn Thr Ser Gly Tyr Ile Leu Asp Pro His Thr
            100                 105                 110

Ala Val Ala Lys Val Val Ala Asp Arg Val Gln Asp Lys Thr Cys Pro
        115                 120                 125

Val Ile Ile Ser Ser Thr Ala His Tyr Ser Lys Phe Ala Pro Ala Ile
    130                 135                 140

Met Gln Ala Leu Lys Ile Lys Glu Ile Asn Glu Thr Ser Ser Ser Gln
145                 150                 155                 160

Leu Tyr Leu Leu Gly Ser Tyr Asn Ala Leu Pro Pro Leu His Glu Ala
                165                 170                 175

Leu Leu Glu Arg Thr Lys Gln Gln Lys Met Glu Tyr Gln Val Cys
            180                 185                 190

Ala Ala Asp Met Asn Val Leu Lys Ser His Val Glu Gln Leu Val Gln
        195                 200                 205

Asn Gln Phe Ile
    210
```

```
-continued

<210> SEQ ID NO 14
<211> LENGTH: 14
<212> TYPE: PRT
<213> ORGANISM: Homo sapiens

<400> SEQUENCE: 14

Cys Ser Asp Thr Ser Pro Asp Thr Glu Glu Ser Tyr Ser Asp
1               5                   10

<210> SEQ ID NO 15
<211> LENGTH: 15
<212> TYPE: PRT
<213> ORGANISM: Homo sapiens

<400> SEQUENCE: 15

Cys Ser Asp Leu Lys Arg Ser Leu Gly Phe Val Ser Lys Val Glu
1               5                   10                  15

<210> SEQ ID NO 16
<211> LENGTH: 9
<212> TYPE: PRT
<213> ORGANISM: Homo sapiens

<400> SEQUENCE: 16

Cys Ala Glu Glu Glu Lys Glu Glu Leu
1               5
```

METHODS AND COMPOSITIONS FOR DIAGNOSING HEPATOCELLULAR CARCINOMA

This application claims the benefit of priority to PCT/US03/20841 filed on Jul. 3, 2003, and to U.S. Provisional Application Ser. No. 60/393,982 filed on Jul. 3, 2003, both of which are hereby incorporated by reference in their entireties.

FEDERALLY SPONSORED RESEARCH OR DEVELOPMENT

This invention was made with Government support under Grant No. U19A148214 from the National Institutes of Health. The Government has certain rights in the invention.

BACKGROUND

The field of the invention is the diagnosis of hepatocellular carcinoma (HCC).

Hepatocellular carcinoma (HCC) is the most prevalent form of liver cancer worldwide. Incidence of the disease varies geographically from between 1 in 5,000 in Asia to 1 in 20,000 in western nations (Wildi et al., 2002). Patients with chronic liver disease are at increased risk for development of hepatocellular carcinoma. This is particularly true for individuals with liver cirrhosis who should be closely monitored for development of this disease.

Currently, it is difficult to diagnose HCC. Methods employed generally rely on imaging techniques such as MRI, CT, and ultrasound and are of little use in detecting the disease in its earliest stages. As with most cancers, early detection of HCC would leave physicians with more treatment options and patients with a better prognosis (Befeler and Bisceglie, 2002).

Better imaging reagents would enhance the sensitivity and broaden the applicability of currently used scanning methodologies. Proteins expressed specifically or preferentially on the surface of HCC cells could be targeted by an antibody or other targeting reagent that is conjugated to an imaging agent. Such conjugates would aid in diagnosis of the disease at an early stage.

The literature describes a few serodiagnostic markers indicative of HCC, including alpha-fetoprotein (AFP), *Lens culinaris* agglutinin-reactive fraction (AFP-L3), and des-gamma-carboxy prothrombin or PIVKA-II (Shimizu et al., 2002; Ikoma et al., 2002; Fujiyama et al., 1986; Naraki et al., 2002). Unfortunately, at best, elevated levels of these serum proteins are detected in only about 50% of HCC patients. A significant increase in the sensitivity of HCC diagnosis can be achieved by combining tests for AFP, AFP-L3 and PIVKA-II. However, even when all three tests are combined, the sensitivity is only about 87% (Fujiyama et al., 2002).

Identification of new serodiagnostic markers specific to HCC and present in a large percentage of HCC patients would greatly improve the diagnosis of this disease and be more cost effective than commonly used scanning methodologies and/or the combined use of all currently available serodiagnostic assays.

These and other limitations and problems of the past are solved by the present invention.

BRIEF SUMMARY OF THE INVENTION

The present invention relates to the detection of hepatocellular carcinoma (HCC) by assaying patient samples such as tissue, plasma, serum, etc. for the presence and level of specific HCC related proteins. Some of these proteins will be cell associated, while others will not be cell associated. A finding of elevated levels of one or more of these proteins in a patient sample indicates that the patient has hepatocellular carcinoma. HCC diagnosis based on quantification of the HCC related protein(s) will be dependent upon research that will define a variety of parameters. These parameters will include: (a) a determination of the relative levels of the HCC related proteins in diseased versus normal patient samples (as an example of a control level, but not limited to), and (b) the specificity, sensitivity and reproducibility of the assay or assays employed.

The present invention also relates to identification of tumor markers that may be targeted by specific reagents to enhance early diagnosis of HCC by traditional scanning methodologies. Proteins expressed specifically on the surface of HCC cells could be targeted by an antibody or other targeting reagent (e.g. soluble receptor or ligand) that binds specifically to the cell-associated HCC protein. The targeting moiety is conjugated to an imaging agent to enable visualization of the construct.

The proteins that are useful in accordance with the present invention are: phospholipase A2 (Group XIII) (SEQ ID Nos. 1-2); phospholipase A2 (group VII) (SEQ ID No. 12); anti-thrombin III (SEQ ID No. 3); apolipoprotein B (SEQ ID No. 4); group C specific vitamin D binding protein (SEQ ID Nos. 5-6); gamma-glutymyl hydrolase (SEQ ID No. 7); nicastrin (SEQ ID No. 8); pregnancy associated plasma protein A, plasma glutamate carboxypeptidase (SEQ ID No. 11); secretory carrier membrane protein-3 (SEQ ID Nos. 9-10); and other hypothetical proteins described herein. Not all of the proteins that are useful within the methods of the present invention are found exclusively in HCC patients. Some proteins will be found in both patents with and without HCC. In these cases, HCC affected individuals will be distinguished from non diseased individuals by a significant elevation in the amount of one or more of the proteins described in the current invention.

The invention will best be understood by reference to the following detailed description of the preferred embodiment. The discussion below is descriptive, illustrative and exemplary and is not to be taken as limiting the scope defined by any appended claims.

DETAILED DESCRIPTION OF THE PREFERRED EMBODIMENT

Expression microarray analysis of tumor samples from Hepatitis C (HCV) infected patients with hepatocellular carcinoma (HCC) led to the identification of genes that were specifically up-regulated in hepatocellular carcinoma tumor tissue when compared to HCV infected cirrhotic non-tumor tissue, and normal liver.

Liver and HCC samples were obtained during surgical procedures with prior informed consent from all persons involved. HCC samples included 21 from HCV infected patients and 1 from a patient infected with Hepatitis B. In addition, 4 samples of normal, non-diseased liver and 8 samples of HCV infected, cirrhotic liver with no evidence of HCC were used for analysis.

Total RNA was isolated as described in Geiss et al. (2001). RNA amplification was performed using a T7 RNA polymerase protocol (Eberwine, 1996) with the AmpliScribe Transcription kit (Epicentre Technologies, Madison, Wis.) as described by the manufacturer. The quality of amplified RNA samples was evaluated using capillary electrophoresis in an Agilent 2100 Bioanalyzer (Agilent Technologies, Palo Alto, Calif.).

cDNA microarrays were constructed by the University of Washington's Center for Expression Array Technology using PCR products generated by amplification of sequence verified I.M.A.G.E. consortium clones obtained from Research Genetics (St. Louis, Mo.) (Lennon et al. 1996). Microarrays were constructed as previously described (Geiss et al. 2001). A human high density set consisted of two arrays, each of which represented 7,296 human clones in duplicate with a number of additional control sequences, for a total of 14,976 clones (approximately 13,597 unique I.M.A.G.E. cDNA clones). Each single experiment involved interrogation of two slides for which the dye labels had been reversed (fluor reversal methodology as described in Geiss et al., 2000; Geiss et al., 2001). A total of at least four separate hybridization measurements were taken per gene per experiment.

Protocols for probe synthesis, microarray hybridization, and wash conditions are as previously described (Geiss et al. 2001). Microarrays were scanned and the images were quantified using a custom spot-finding program, Spot-On Image (Geiss et al, 2000 and Geiss et al., 2001), that calculated the standard deviations and the mean ratios between the expression levels of each gene in the analyzed pair of samples. Raw data and sample information were entered into a custom designed database, Expression Array Manager, and evaluated using Rosetta Biosoftware's Resolver® Version 3.0 (Rosetta Biosoftware, Kirkland, Wash.), a software package for the storage and analysis of microarray expression data. This package implements common statistical procedures (clustering, trend analysis, similarity searches based on a BLAST-related algorithm, etc.) together with a sophisticated error model to compensate for biological and experimental variation.

The expression microarray data was processed by two different methods. The first involved examining only HCV-infected HCC patient samples and sorting for genes that were significantly ($p<0.01$) up-regulated more than two-fold in tumor versus non-tumor liver samples from the same patient. Genes that met these criteria in ten or more patients were then analyzed relative to samples from HCV infected patients with liver cirrhosis but no tumors and also relative to samples of normal healthy liver. If the gene was unchanged or down-regulated in these control samples, its potential for use as a diagnostic target was further evaluated using information available in the National Center for Biotechnology Information databases (Unigene, OMIM, LocusLink, and HomoloGene) and currently published literature regarding the location and function of its protein product. The protein products of the genes that meet the above criteria and are (a) secreted or likely to be present on the plasma membrane and are (b) noted to be preferentially or specifically expressed in liver, are likely to be diagnostic indicators of HCC. The following are an example of some of these proteins while their corresponding amino acid sequences and variants thereof are included in the sequence listing accompanying this application:

PGLA2G13 (phospholipase A2 Group XIII; IMAGE EST: 297107; GenBank AF349540; Unigene: 333175; mRNA: NM 032562; protein: NP 115951; (SEQ ID Nos. 1-2));

SERPINC1 (serine or cysteine proteinase inhibitor; anti thrombin III; IMAGE EST:85643; GenBank X68793; Unigene: Hs.75599; mRNA: 000488; protein: NP 000479; (SEQ ID No. 3));

APOB (apclipoprotein B; IMAGE EST: 206632; GenBank X04506; Unigene: Hs.585; mRNA: NM 000384; protein: NP 000375; (SEQ ID No. 4));

GC (group C specific vitamin D binding protein; IMAGE EST: 195340; GenBank M12654; Unigene: Hs.198246; mRNA: NM 000583; protein: NP 000574; (SEQ ID Nos. 5-6));

GGH (gamma-glutymyl hydrolase; conjugase; folylpolyga-mmaglutamyl hydrolase; IMAGE EST: 809588; GenBank U55206; Unigene: Hs.78619; mRNA: NM 003878; protein: NP 003869; (SEQ ID No. 7)); and NCSTN (nicastrin; IMAGE EST: 199645; GenBank R96527; Unigene: Hs.4788; (SEQ ID No. 8)).

The function of a number of genes that were up-regulated in the HCC samples but not in control samples is unknown. Included herein are the protein products of these genes and their use as diagnostic markers for HCC. These gene products are as follows:

Protein coded by the gene specified as: IMAGE EST: 241475; GenBank H90421; Unigene: Hs.41407;

Protein coded by the gene specified as: IMAGE EST: 293094; GenBank N91620; Unigene: Hs.12160;

Protein coded by the gene specified v: IMAGE EST: 430221; GenBank AA100360; Unigene: Hs.60380;

Protein coded by the gene specified as: IMAGE EST: 52990; GenBank R15441; Unigene: Hs.4774;

Protein coded by gene specified as: IMAGE EST: 153779; GenBank R48248; Unigene: Hs.183171; mRNA: NM 024838; protein: NP 079114 hypothetical protein FLJ22002; (SEQ ID No. 13).

The second method of processing the microarray data yielded similar results. Error probabilities were used to filter the initial 13,597 member gene set to a set of 2302 genes that demonstrated differential regulation of two-fold or greater with 95% confidence ($p<=0.05$) in at least 4 out of 20 experiments involving the comparison of HCC tumor versus matched non-tumor tissues. A keyword search was then applied to this group to identify genes encoding putative secreted and/or plasma membrane proteins. The resultant small gene subset was manually filtered to exclude those genes that were down-regulated in most tumors. Finally, a set of 11 genes was selected and used for two dimensional clustering analyses of all 4 experiments. Four out of 11 genes showed a pronounced up-regulation of gene expression in about 60 to 70% of all tumor versus non-tumor liver experiments. Also, all four genes were significantly up-regulated in experiments involving pooled tumor versus normal liver samples. The four gene products are listed below and include several of the proteins noted above.

Corresponding amino acid sequences and variants thereof are listed in the sequence listing accompanying this patent.

SCAMP3 (secretory carrier membrane protein-3; IMAGE EST: 156045; GenBank R72518, Unigene: Hs.200600; mRNA: NM 005698; protein: NP 005689; (SEQ ID Nos. 9-10));

PGCP (plasma glutamate carboxypeptidase; IMAGE EST: 796263; Unigene: Hs.197335; (SEQ ID No. 11)) Gingras et al. 1999;

PGLA2G13 (phospholipase A2 Group XIII; IMAGE EST: 297107; GenBank AF349540; Unigene: 333175; mRNA: NM 032562; protein: NP 115951; (SEQ ID Nos. 1-2)); and PLA2G7 (phospholipase A2 group VII; IMAGE EST: 238821; GenBank H65029; Unigene: Hs.93304; mRNA: NM 005084; protein: NP 005075; (SEQ ID No. 12)).

Several of the proteins that were identified by either method will find use for the diagnosis of HCC. An elevated level of one or more of these proteins in a patient sample is indicative of disease. Diagnostic proteins are expressed in either a cell associated or non-cell associated way. The method of diagnosis will depend on whether the diagnostic or predictive protein is cell associated or non-cell associated.

The non-cell associated proteins include PGCP (SEQ ID No. 11), PGLA2G13 (SEQ ID Nos. 1-2), PLA2G7 (SEQ ID No. 12), SERPINC1 (SEQ ID No. 3), APOB (SEQ ID No. 4), GC (SEQ ID Nos. 5-6), and GGH (SEQ ID No. 7). The diagnosis of HCC may result from quantification of these proteins individually or in combination in patient samples such as blood, plasma, serum, urine, etc.

The presence and quantity of non-cell associated proteins within a patient sample will be measured by state of the art techniques which include, but are not limited to, ELISA, sandwich ELISA, radiolabeled immunoassay (RIA) or other competitive binding assay that is based on the use of specific antibodies. Alternatively, activity assays for quantification of those non-cell associated proteins that are enzymes (PGCP (SEQ ID No. 11); PLA2G7 (SEQ ID No. 12); PLA2G13 (SEQ ID Nos. 1-2); SERPINC1 (SEQ ID No. 3); and GGH (SEQ ID No. 7)) may also be employed.

In addition or in the alternative, HCC may be diagnosed by imaging or scanning methodologies employing targeting agent-imaging agent conjugates. Preferred proteins for this aspect of the present invention are the cell associated proteins, SCAMP3 (SEQ ID Nos. 9-10) and NCSTN (SEQ ID No. 8), and will find use as imaging targets when used in combination with labeling and scanning technologies.

The targeting agents useful in the practice of the present invention include, but are not limited to, antibodies or soluble receptors or ligands or other agents that specifically bind proteins expressed by HCC cells. When conjugated to imaging agents, these targeting agents enable visualization of tumor cells.

The imaging agents useful in the practice of the present invention include, but are not limited to, radioisotopes, electron dense dyes and/or a variety of other reagents visible to scanning technologies that have been well described in the literature (see for example: Vera et al. 1995; Shen et al. 1996; Matsumura et al. 1994; Reimer et al. 1994; Koral et al. 1994; Winzelberg et al. 1992; Perkins et al. 1993).

The targeting molecule-imaging agent-conjugate will be administered to the patient intravenously prior to employment of the imaging application thereby enabling and/or enhancing tumor visualization. The molecular imaging agent-conjugate may bind to the cell associated HCC related protein or may be subject to receptor mediated uptake where the receptor is the cell associated HCC related protein.

Other methods of the present invention involve the use of liver tissue samples. For these aspects of the present invention, the patient sample may be obtained by biopsy or other technique known in the art.

An embodiment of the present invention useful in the analysis of tissue samples includes employing immunocytochemistry or immunohistochemistry techniques using a cell-associated HCC related protein specific antibody conjugated to imaging agents.

In addition, tissue samples may be evaluated by assaying for transcription of one or more of the cell-associated or non-cell associated HCC related proteins by RT-PCR or nucleic acid hybridization methods.

The diagnosis of HCC may result from quantification of these proteins individually or in combination using any of the methods noted above.

Of direct relevance herein are the development of polyclonal antibodies which bind to recombinant human PLA2G13 (SEQ ID Nos. 1-2) and the use of said antibodies in quantification or visualization of PLA2G13 (SEQ ID Nos. 1-2). The generation of polyclonal antisera by immunization of rabbits and the use of Western Blot analysis, as outlined below, will be familiar to one skilled in the art.

Polyclonal antibodies were generated by immunizing rabbits with either the recombinant human PLA2G13 (variant 1; SEQ ID No. 1) or with synthetic peptides (SEQ ID Nos. 14-16) representing portions of human PLA2G13 (SEQ ID No. 1) coupled to a carrier protein. The sequence of each of these peptides is indicated below with an additional cysteine residue added to the 5'-terminus of peptide #1 as a means of conjugation to the carrier protein.

(SEQ ID No. 14) Peptide #1: 5' CSDTSPDTEESYSD 3'

(SEQ ID No. 15) Peptide #2: 5' CSDLKRSLGFVSKVE 3'

(SEQ ID No. 16) Peptide #3: 5' CAEEEKEEL 3'

Antisera from rabbits immunized with recombinant human PLA2G13 (SEQ ID No. 1) or with carrier protein conjugates of peptides #1 or #3 contained antibodies that bound recombinant human PLA2G13 (SEQ ID No. 1). This was verified by a Western Blot Assay.

The recombinant human PLA2G13 (SEQ ID No. 1) used in Western Blot Assay was expressed in, and purified from *E. coli* using known molecular biological and biochemical methods as outlined in Koduri et al. (2002) for a similar protein. Additionally, the recombinant human PLA2G13 (SEQ ID No. 1) was refolded as and characterized as described for a similar protein by Valentin et al., 1999, indicating that it is in its native conformation. Polyclonal antibodies that bind the recombinant human PLA2G13 (SEQ ID No. 1) in a native conformation will likely bind endogenous or native PLA2G13 (SEQ ID No. 1-2) in humans or human derived material. The generation of polyclonal antibodies that bind PLA2G13 (SEQ ID No. 1) enables the development of antibody based assays to detect endogenous PLA2G13 (SEQ ID Nos. 1-2) in patients or detect and quantify PLA2G13 (SEQ ID Nos. 1-2) in patient derived material. Additionally, the anti-PLA2G13 (SEQ ID No. 1) antibodies can serve as the targeting portion of imaging conjugate(s).

The discussion above is descriptive, illustrative and exemplary and is not to be taken as limiting the scope defined by any appended claims.

REFERENCES

1) Fujiyama, S. et al. (2002) Oncology 62 (suppl 1): 57-63
2) Befeler, A. S. and Bisceglie, A. M. (2002) Gastroenterol. 122: 1609-1619
3) Eberwine, J. (1996) Biotechniques 20: 584-591
4) Fujiyama et al. (1986) Hepatogastroenterol. 33: 201-205
5) Geiss, G. K. et al. (2000) Virol. 266: 8-16
6) Geiss, G. K. et al. (2001) J. Virol. 75: 4321-4331
7) Gingras, R. et al. (1999) J. Biol. Chem. 274: 11742-11750
8) Ikoma, J. et al. (2002) Hepatogastroenterol. 49: 235-238
9) Koduri, R. S. et al. (2002) J. Biol. Chem. 277: 5849-5857
10) Koral, K. F. (1994) J. Nucl. Med. 35: 1714-1720
11) Lennon, G. et al. (1996) Genomics 33 (1): 151-15

12) Matsumura, A. et al. (1994) Acta Neurochir. Suppl (WEIN) 60: 356-358
13) Naraki, T. et al. (2002) BBA 1586: 287-298
14) Orci, L. et al. (1989) Science 245: 295-297
15) Perkins, A. C. (1993) Nucl. Med. Commun. 14: 578-586
16) Reimer, P. et al. (1994) Radiology 193: 527-531
17) Shen, T. T. et al. (1996) Bioconjug. Chem. 7: 311-316
18) Shimizu, A. (2002) International J. Mol. Med. 9: 245-250
19) Valentin, E. et al. (1999) J. Biol. Chem. 274: 19152-19160
20) Vera, D. R. et al. (1995) Acad. Radiol. 2: 497-506
21) Winzelberg, G. G. (1992) 69: 1656-1663
22) Wildi, S. et al. (2002) Swiss Surg. 8: 61-66

We claim:

1. A method of detecting the presence of HCC in a mammal comprising:
    a) obtaining a biological sample from the mammal;
    b) assaying the sample to quantify a non-cell-associated HCC related protein;
    c) comparing the quantity of the non-cell-associated HCC related protein to a control level obtained from a sample without HCC, wherein the non-cell-associated HCC related protein comprises phospholipase A2 group XIII (PLA2G13); and
    d) detecting the presence of HCC in said mammal if PLA2G13 is elevated in step c) above.

2. The method of claim 1 wherein assaying the sample is selected from the group consisting of using an enzyme linked immunosorbent assay (ELISA) and competition assays using monoclonal, polyclonal, or a combination of monoclonal and polyclonal antibodies.

3. The method of claim 2 wherein the polyclonal antibodies include those that bind PLA2G13.

* * * * *

UNITED STATES PATENT AND TRADEMARK OFFICE
CERTIFICATE OF CORRECTION

PATENT NO. : 7,588,902 B2 Page 1 of 1
APPLICATION NO. : 10/520322
DATED : September 15, 2009
INVENTOR(S) : Michael Katze et al.

It is certified that error appears in the above-identified patent and that said Letters Patent is hereby corrected as shown below:

Title Pg, Item (73) Assignee: should read
--(73) Assignee: Illumigen Biosciences, Inc., Seattle, WA (US)
University of Washington, Seattle, WA (US)--.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,588,902 B2 |
| APPLICATION NO. | : 10/520322 |
| DATED | : September 15, 2009 |
| INVENTOR(S) | : Katze et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 727 days.

Signed and Sealed this

Twenty-first Day of September, 2010

David J. Kappos
*Director of the United States Patent and Trademark Office*